(12) United States Patent
Rich et al.

(10) Patent No.: US 11,830,592 B2
(45) Date of Patent: Nov. 28, 2023

(54) MACHINE LEARNING MODEL FOR EXTRACTING DIAGNOSES, TREATMENTS, AND KEY DATES

(71) Applicant: Flatiron Health, Inc., New York, NY (US)

(72) Inventors: Alexander Rich, Brooklyn, NY (US); Barry Leybovich, Brooklyn, NY (US); Benjamin Irvine, New York, NY (US); Nisha Singh, South Richmond Hill, NY (US); Benjamin Birnbaum, Brooklyn, NY (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 17/686,824

(22) Filed: Mar. 4, 2022

(65) Prior Publication Data

US 2022/0284999 A1 Sep. 8, 2022

Related U.S. Application Data

(60) Provisional application No. 63/157,369, filed on Mar. 5, 2021.

(51) Int. Cl.
*G16H 10/60* (2018.01)
(52) U.S. Cl.
CPC .................................. *G16H 10/60* (2018.01)
(58) Field of Classification Search
CPC ...................................................... G16H 10/60
See application file for complete search history.

(56) References Cited

U.S. PATENT DOCUMENTS

| 2016/0110501 | A1* | 4/2016 | Allen | G16Z 99/00 |
| | | | | 705/3 |
| 2017/0024388 | A1* | 1/2017 | Bentley | G06F 16/9537 |
| 2020/0218744 | A1* | 7/2020 | Wang | G16H 10/60 |
| 2020/0387570 | A1* | 12/2020 | Biswas | G06F 40/30 |

(Continued)

FOREIGN PATENT DOCUMENTS

| WO | WO 2020/081495 A1 | 4/2020 |
| WO | WO 2020/092316 | 5/2020 |

OTHER PUBLICATIONS

International Search Report and Written Opinion issued in PCT Application No. PCT/US2022/018920 dated Jun. 8, 2022 (11 pages).

(Continued)

*Primary Examiner* — Mark Holcomb
(74) *Attorney, Agent, or Firm* — FINNEGAN, HENDERSON, FARABOW, GARRETT & DUNNER, LLP

(57) ABSTRACT

A model-assisted system for determining a patient event date may include a processor. The processor may be programmed to access a database storing a medical record associated with a patient, the medical record comprising unstructured data; analyze the unstructured data to identify a plurality of snippets of information in the medical record associated with a patient event; determine a date associated with each of the plurality of snippets, identify a plurality of query periods associated with the patient event; and generate, for each of the query periods, a probability of whether the patient event occurred during the query period based on the plurality of snippets and the associated dates.

19 Claims, 8 Drawing Sheets

(56) References Cited

U.S. PATENT DOCUMENTS

2021/0027894 A1    1/2021    Rich et al.
2021/0090747 A1*  3/2021    Birnbaum .............. G06N 20/00

OTHER PUBLICATIONS

Zhao Shiyi et al., "Associative Attention Networks for Temporal Relation Extraction from Electronic Health Records," Journal of Biomedical Informatics, Academic Press, New York, NY, vol. 99, Oct. 15, 2019 (9 pages).

* cited by examiner

MACHINE LEARNING MODEL FOR EXTRACTING DIAGNOSES, TREATMENTS, AND KEY DATES

CROSS REFERENCE TO RELATED APPLICATION

This application is based on and claims the benefit of priority of U.S. Provisional Application No. 63/157,369, filed on Mar. 5, 2021. The contents of the foregoing application are incorporated herein by reference in their entirety.

BACKGROUND

Technical Field

The present disclosure relates to the analysis of medical records and, more specifically, to the extraction of key dates and other information from unstructured medical data.

Background Information

In today's health care system, analyzing patient diagnosis, treatment, testing, and other healthcare data across large populations of patients can provide helpful insights for understanding diseases, for the development of new forms of therapies and treatments, and for evaluating the efficacy of existing therapies and treatments. In particular, it may be helpful to identify particular dates associated with key events or stages within the course of a patient's diagnosis and/or treatment. For example, it may be beneficial for researchers to identify patients diagnosed with a particular disease as well as the date at which the disease was diagnosed or a date associated with a particular stage of the disease. It may further be beneficial to extract other dates, such as a date of a later advanced diagnosis (e.g., due to a recurrence or advanced stage of a disease). This may allow researchers to make determinations across large populations of patients in order to, for example, select patients for inclusion in a clinical trial.

Patient information may be included in electronic medical records (EMRs). However, in many cases, information regarding diagnosis dates or other key events is represented in unstructured data (e.g., doctors' visit notes, lab technician reports, or other text-based data), which can make computer-based extraction of relevant date information difficult. For example, a doctor may include notes referring to a medical diagnosis in several documents within a patient's medical record without explicitly including a date of diagnosis. Accordingly, determining a precise date of a diagnosis (or similar event) based on ambiguous notes may involve piecing together several snippets of information. Further, the sheer volume of data that a researcher would have to review makes manual extraction of dates or other information infeasible. For example, this may include searching though thousands, tens of thousands, hundreds of thousands, or millions of patient medical records, each which may include hundreds of pages of unstructured text. Accordingly, it can be very time consuming and arduous, if not impossible, for human reviewers to process this amount of data. Therefore, using conventional techniques, extracting key dates from patient medical records, especially for large groups of patients, may quickly become an unsurmountable task.

Accordingly, in view of these and other deficiencies in current techniques, technical solutions are needed to more accurately extract key dates associated with diagnosis and treatment of patients. In particular, solutions should advantageously allow particular dates (e.g., dates of initial diagnosis, dates of advanced diagnoses, start date of treatment, end date of treatment, etc.) to be extracted from unstructured data in large sets of patient EMRs.

SUMMARY

Embodiments consistent with the present disclosure include systems and methods for determining a patient event date. In an embodiment, a model-assisted system may comprise a least one processor. The processor may be programmed to access a database storing a medical record associated with a patient, the medical record comprising unstructured data; analyze the unstructured data to identify a plurality of snippets of information in the medical record associated with a patient event; determine a date associated with each of the plurality of snippets; identify a plurality of query periods associated with the patient event; and generate, for each of the query periods, a probability of whether the patient event occurred during the query period based on the plurality of snippets and the associated dates.

In an embodiment, a method for determining a patient event date is disclosed. The method may include accessing a database storing a medical record associated with a patient, the medical record comprising unstructured data; analyzing the unstructured data to identify a plurality of snippets of information in the medical record associated with a patient event; determining a date associated with each of the plurality of snippets; identifying a plurality of query periods associated with the patient event; and generating, for each of the query periods, a probability of whether the patient event occurred during the query period based on the plurality of snippets and the associated dates.

Consistent with other disclosed embodiments, non-transitory computer readable storage media may store program instructions, which are executed by at least one processor and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings.

DETAILED DESCRIPTION

Figure 1:
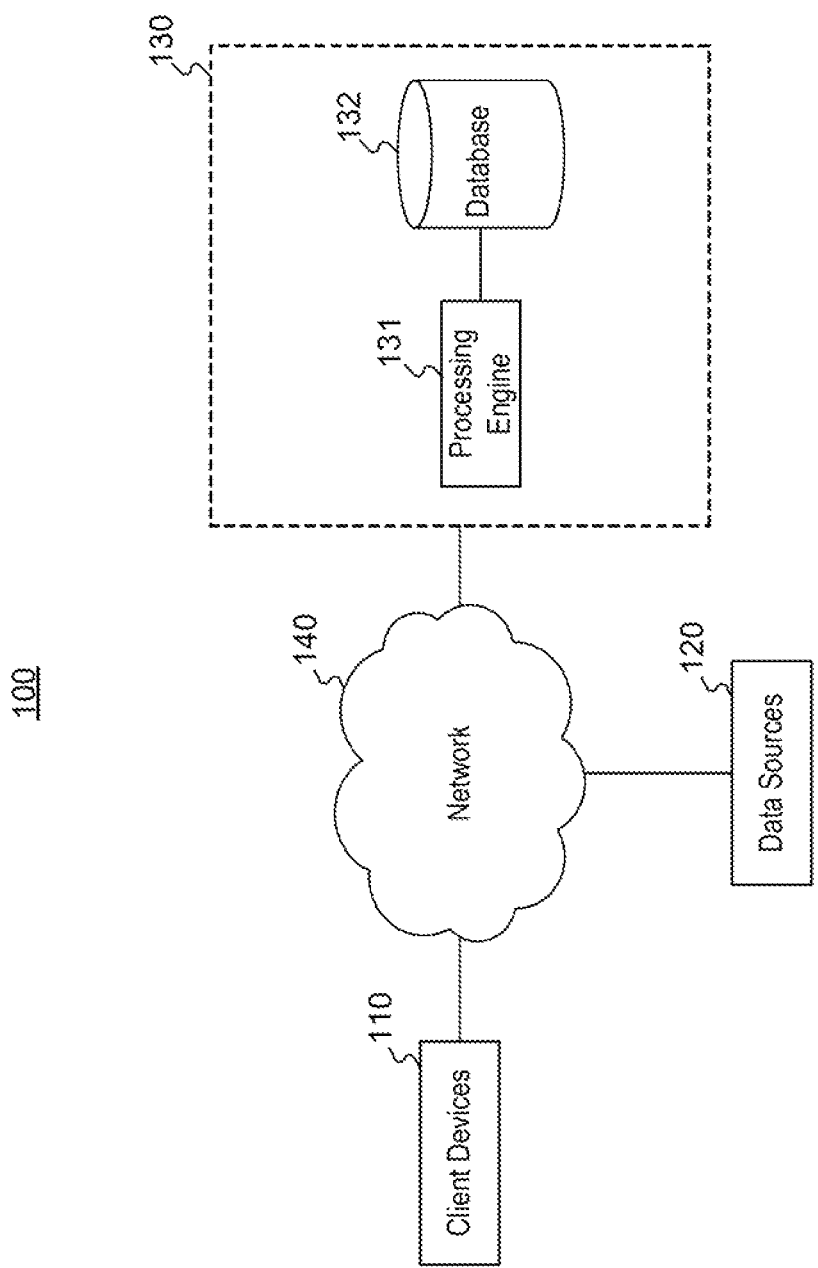
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments disclosed herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Disclosed systems and methods may automate the analysis of medical records of a patient or patient population to identify dates associated with key events during the diagnosis and treatment of a patient. For example, researchers, physicians, clinicians, or other users may be interested in identifying patients diagnosed with a particular disease as well as an estimated date of the diagnosis, or patients being treated with a particular medication and dates associated with such treatment. This may allow users to efficiently make various determinations about individual patients within large populations based on analysis of EMRs. For example, a researcher may identify patients that have been diagnosed with an advanced stage of a disease and the date of the advanced diagnosis, which may indicate whether the patients may be eligible for inclusion in a clinical trial or other form of cohort.

FIG. 1 illustrates an example system environment 100 for implementing embodiments consistent with the present disclosure, described in detail below. As shown in FIG. 1, system environment 100 may include several components, including client devices 110, data sources 120, system 130, and network 140. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 may include a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 131 and one or more databases 132, which are illustrated in a region bounded by a dashed line representing system 130. Processing engine 131 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse. A user of system environment 100 may encompass any individual who may wish to access and/or analyze patient data. Thus, throughout this disclosure, references to a "user" of the disclosed embodiments may encompass any individual, such as a physician, a researcher, a quality assurance department at a health care institution, and/or any other individual.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

The components of environment 100 (including system 130, client devices 110, and data sources 120) may communicate with each other or with other components through network 140. Network 140 may comprise various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols.

System 130 may be configured to receive and store the data transmitted over network 140 from various data sources, including data sources 120, process the received data, and transmit data and results based on the processing to client device 110. For example, system 130 may be configured to receive patient data from data sources 120 or other sources in network 140. In some embodiments, the patient data may include medical information stored in the form of one or more medical records. Each medical record may be associated with a particular patient. Data sources 120 may be associated with a variety of sources of medical information for a patient. For example, data sources 120 may include medical care providers of the patient, such as physicians, nurses, specialists, consultants, hospitals, clinics, and the like. Data sources 120 may also be associated with laboratories such as radiology or other imaging labs, hematology labs, pathology labs, etc. Data sources 120 may also be associated with insurance companies or any other sources of patient data.

System 130 may further communicate with one or more client devices 110 over network 140. For example, system 130 may provide results based on analysis of information from data sources 120 to client device 110. Client device 110 may include any entity or device capable of receiving or transmitting data over network 140. For example, client device 110 may include a computing device, such as a server or a desktop or laptop computer. Client device 110 may also include other devices, such as a mobile device, a tablet, a wearable device (i.e., smart watches, implantable devices, fitness trackers, etc.), a virtual machine, an IoT device, or other various technologies. In some embodiments, client device 110 may transmit queries for information about one or more patients over network 140 to system 130, such as a query for patients having or being associated with a particular attribute, a date that patients were associated with an attribute, a date of an event associated with the patient, or various other information about a patient.

In some embodiments, system 130 may be configured to analyze patient medical records (or other forms of unstructured data) to determine dates associated with key events during the diagnosis and/or treatment of a patient. For example, system 130 may analyze medical records of a patient to determine a date the patient has been diagnosed with a particular condition (e.g., metastasis in a particular region of the body), a date of a test for a particular condition, a date the patient tested positive or negative for a particular condition, a begin or end date of a particular treatment or type of treatment (e.g., taking a particular drug, etc.), a date of an operation (e.g., a date of a surgery, etc.), or various other dates. System 130 may be configured to use one or more machine learning models to perform this analysis, as described further below. While patient medical records are used as an illustrative example throughout the present disclosure, it is understood that in some embodiments, the disclosed systems, methods, and/or techniques may similarly be used to identify patients exhibiting conditions from other forms of records.

In order to efficiently extract a particular disease or treatment along with key dates and stages associated with the disease or treatment, system 130 may be configured to access a database storing medical records associated with one or more patients. A medical record may refer to any form of document including data regarding diagnosis and/or treatment of a patient. In some embodiments, a patient may be associated with more than one medical record. For example, a doctor associated with the patient, a nurse associated with the patient, a physical therapist associated with the patient, pathologist, radiologist, or the like, may each generate a medical record for the patient.

Figure 2:
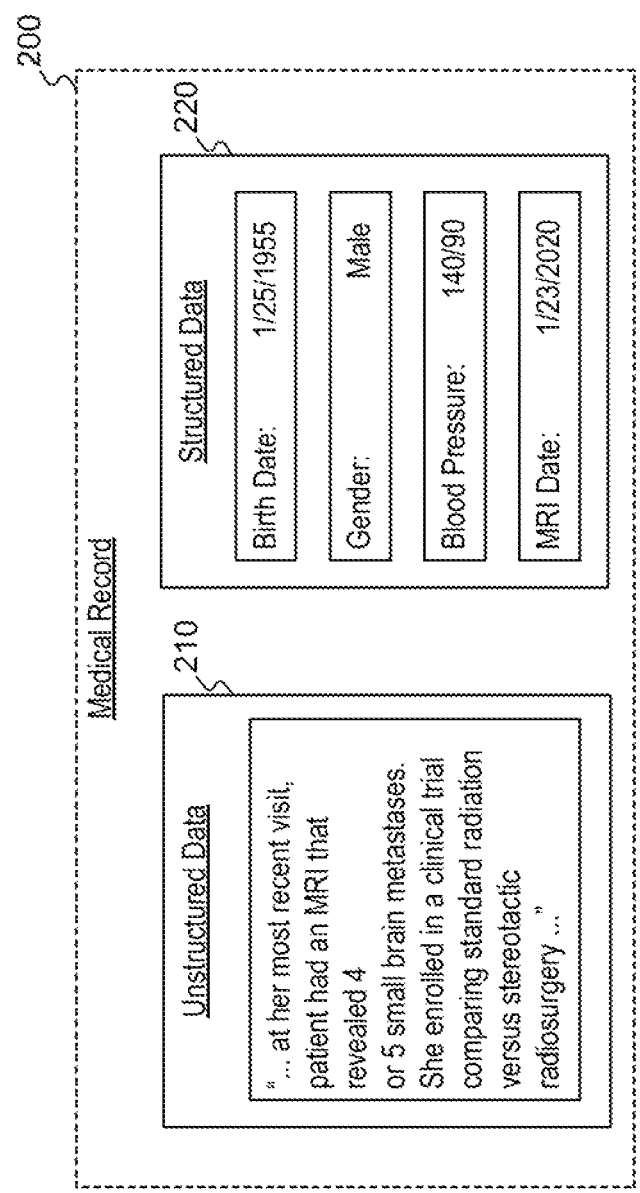
FIG. 2 is a block diagram illustrating an exemplary medical record for a patient, consistent with the disclosed embodiments.

FIG. 2 is a block diagram illustrating an exemplary medical record 200 for a patient, consistent with the disclosed embodiments. Medical record 200 may be received from data sources 120 and processed by system 130 to identify dates associated with a patient, as described above. The records received from data sources 120 (or elsewhere) may include one or both of unstructured data 210 and structured data 220, as shown in FIG. 2. Structured data 220 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient.

As described above, much of the information relative to making determinations about a patient, such as dates of treatment or diagnosis, may be stored in unstructured data of a patient medical record. As used herein, unstructured data may include information about the patient that is not quantifiable or easily classified, such as physician's notes or the patient's lab reports. For example, unstructured data 210 may include information such as a physician's description of a treatment plan, notes describing what happened at a visit, statements or accounts from a patient, subjective evaluations or descriptions of a patient's well-being, radiology reports, pathology reports, laboratory reports, or any other forms of information not stored in a structured format.

In the data received from data sources 120, each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases. In some embodiments, the records may be stored and/or provided a plurality of electronic data representations. For example, the patient records may be represented as one or more electronic tiles, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, the unstructured data may be captured by an extraction process, while the structured data may be entered by the health care professional or calculated using algorithms.

In some embodiments, the unstructured data may include data associated with particular patient conditions. As used herein, a "condition" of a patient may refer to any attribute or characteristic associated with the health or wellbeing of a patient. For example, the condition may refer to a diagnosed condition of a patient, such as whether the patient has been diagnosed with a particular illness or disease. In some embodiments, the condition may refer to a stage or status of a particular diagnosed condition. For example, for a patient diagnosed with cancer, the condition may be a particular site of metastasis of the cancer (e.g., whether the patient has been diagnosed with metastasis in the brain, liver, bones, lungs, adrenal gland, peritoneum, or various other sites of metastases).

System 130 may be configured to extract dates associated with various patient conditions. For example, this may include a date the condition developed, was observed, tested for, diagnosed, treated, or any other dates associated with a condition. For example, the date may be a start or end date of a particular line of treatment or therapy for a patient. As used herein, a line of therapy (or line of treatment) may refer to a therapy employed to treat a particular disease or condition. For example, a line of therapy may include administration of a particular drug to a patient (e.g., pharmacotherapy, chemotherapy, etc.), a surgical procedure, a gene therapy, an immunotherapy, changes to a patient's diet, radiation therapy, physiotherapy, counseling or psychotherapy, meditation, sleep therapy, or various other forms of treatment that may be prescribed for a patient. In some embodiments, a date of interest may vary depending on a particular application, such as a type of cohort being selected, a type of research, a type of condition being analyzed, or various other factors.

In many cases, diagnosis information for a particular disease, or a stage of the disease or treatment information for a particular treatment and key dates may be represented within the unstructured data and may not be explicitly tied to a particular date within the patient's medical record. For example, regarding a patient's diagnosis for metastatic non-small cell lung cancer (NSCLC), a physician may refer to the diagnosis in multiple notes before and after the diagnosis date. For example, prior to the advanced diagnosis, a physician may include notes such as "presents with NSCLC, no evidence of metastases" and "possible mets to liver." Various documents subsequent to the advanced diagnosis may include phrases such as "biopsy shows metastases to liver" and "patient with metastatic NSCLC." Thus, using conventional techniques, it may be difficult for an automated system to ascertain the exact date of the advanced diagnosis or the stages of the disease based on the notes. Similar issues may arise for treatment information associated with the disease. For example, prior to beginning a particular treatment for a disease, a physician may include notes indicating a diagnosis of the disease and/or notes indicating various treatment options were discussed with the patient. Subsequent to beginning a treatment, documents in the patient's record may indicate a response to the treatment but may not indicate a particular date on which the treatment began. Therefore, extracting exact dates of treatments may also be difficult using conventional techniques.

To overcome these and other difficulties, system 130 may extract snippets of text related to an event of interest. As discussed above, system 130 may be configured to determine dates associated with a particular event or condition. Following the example of a patient's diagnosis date for metastatic non-small cell lung cancer described above, this may include the snippets "presents with NSCLC, no evidence of metastases," "possible mets to liver," "biopsy shows metastases to liver," and "patient with metastatic NSCLC." In some embodiments, system 130 may perform a search on a set of documents (which may be a set of patient medical records) for keywords associated with a particular event or condition. For example, system 130 may perform a search 510 on one or more unstructured medical record documents to extract snippets associated with diagnosis date for a patient condition. In the case of NSCLC diagnosis, the relevant terms may include "NSCLC," "lung cancer," "mets," "metastases," "metastatic," "spread," or various other words, symbols, acronyms, or phrases that may be associated with a particular event. These sentences or snippets may then be tokenized and represented as a series of tokenized vectors. These tokenized vectors may be processed to generate corresponding vectorized sentences.

Figure 3:
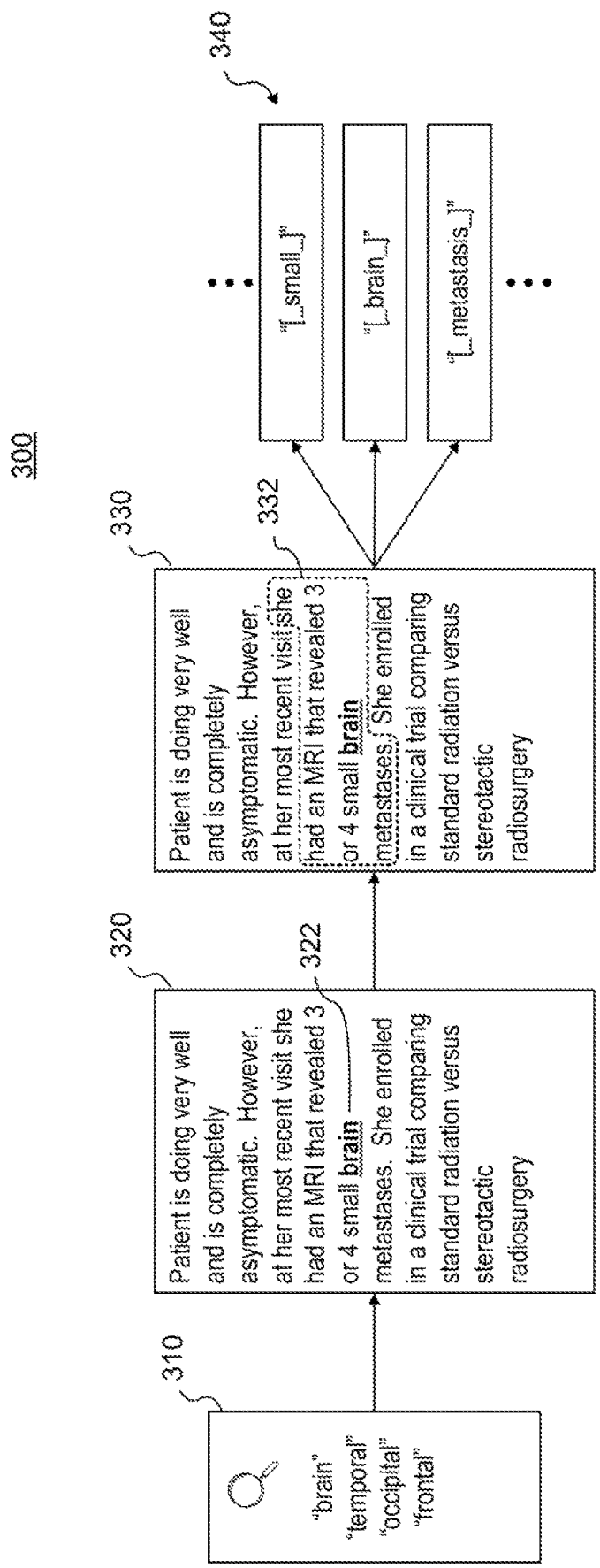
FIG. 3 illustrates an example process for extracting snippets of text in unstructured data of patient medical records, consistent with the disclosed embodiments.

FIG. 3 illustrates an example process 300 for extracting snippets of text in unstructured data of patient medical records, consistent with the disclosed embodiments. In step 310, system 130 may perform a search on a set of documents for keywords associated with a particular event or condition. In this example, a date of interest may be a date of diagnosis for metastases to the brain. Accordingly, the key words may include "brain," "temporal," "occipital," "frontal," or other terms that may be commonly associated with the brain. Accordingly, system 130 may identify term 322 within unstructured text as shown in step 320. System 130 may then extract snippets of text surrounding the relevant terms in the unstructured data. For example, as shown in step 330, snippet 332 surrounding term 322 may be extracted from the unstructured text. The length or structure of the snippet may be specified in various ways. In some embodiments, snippet 332 may be defined based on a predefined window. For example, the snippet may be defined based on a predetermined number of characters before and after target term 322 in the text (e.g., 20 characters, 50 characters, 60 characters, or any suitable number of characters to capture context for use of the term). The window may also be defined to respect word boundaries such that partial words are not included in the edges of the snippet, for example, by expanding or narrowing the window to end at word boundaries or sentence boundaries (e.g., based on punctuation, etc.). In some embodiments, the window may be defined based on a predefined number of words, or other variables.

These sentences or snippets may then be tokenized and represented as a series of tokenized vectors 340. For example, system 130 may replace term 322 with a tokenized term. This may ensure that the patient condition is expressed using the same terminology in each of the extracted snippets. For example, documents including "brain" and documents including "cerebrum" may both result in extracted snippets including the term "[_brain_]," or a similar token. The use of a token may also improve performance of a machine learning model by reducing feature sparsity, speeding up training time, and allowing the model to converge with more limited sets of labeled data. The same tokenization process may be performed for other words within the snippet such that each word is represented by a token. Thus, each snippet can be expressed as a vector of values, with each of the values being a tokenized representation of a word included in the snippet. In some embodiments the snippet vectors may have a predetermined size such that extracted snippets have a uniform size. As a result, a tokenized snippet vector 340 may be extracted from the document. In some embodiments, this may involve applying a gated recurrent unit (GRU) network followed by an attentional layer and a feedforward layer. An example process for generating these snippet vectors is described in U.S. Patent Publication No. 2021/0027894 A1 and PCT International Publication No. WO 2020/092316, which are assigned to the same applicant as the present application. The contents of these applications are hereby incorporated by reference herein in their entirety. These resulting snippet vectors may be input into a trained machine learning model as input vectors.

Figure 4:
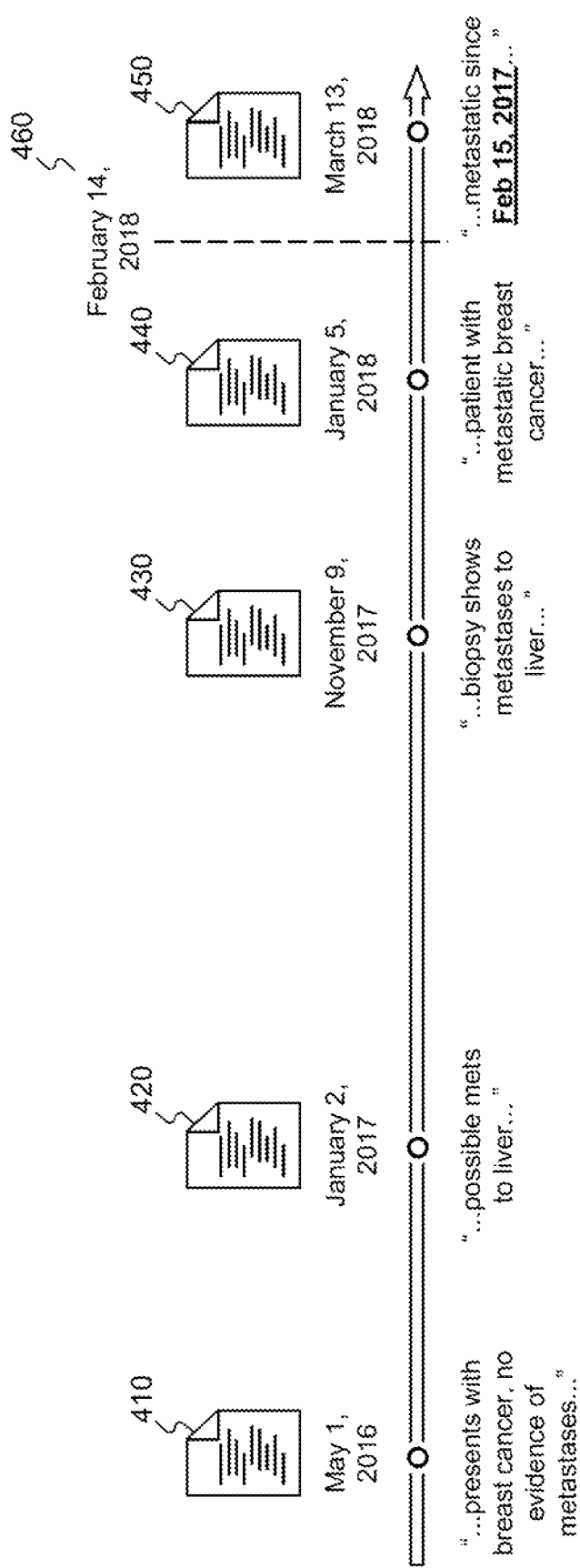
FIG. 4 illustrates an example set of documents that may be analyzed to determine a date associated with a patient, consistent with the disclosed embodiments.

The system may further associate each input vector (i.e., vectorized sentence) with a date. In some embodiments, this may include a date associated with a document from which the snippet was extracted. Alternatively or additionally, various other dates may be associated with each input vector. For example, if the text within or surrounding a snippet includes a particular date, that date may be used in place of a document date. FIG. 4 illustrates an example set of documents that may be analyzed to determine a date associated with a patient, consistent with the disclosed embodiments. In this example, a set of documents 410, 420, 430, 440, and 450 may be analyzed to determine a date that a patient was diagnosed with or developed a liver metastasis. For purposes of illustration, documents 410, 420, 430, 440, and 450 are shown along a timeline 400 corresponding to the document date for each document. Each of documents 410, 420, 430, 440, and 450 may be associated with a document date. The document date may refer to a date the document was created and may be extracted from metadata or other data associated with the document. The document date may refer to various other dates associated with the document, such as a date the document was updated, a revision date, a filing date, a publication date, or any other relevant date. For example, document 410 may be associated with a date of May 1, 2016, and thus a snippet extracted from document 410 may be associated with this date.

In some embodiments, various other dates may be associated with a snippet. For example, if the text within or surrounding a snippet includes a particular date, that date may be used in place of a document date. As shown in FIG. 4, document 450 may include a snippet of "metastatic since Feb. 15, 2017." Although document 450 is dated Mar. 13, 2018, the February 2017 date may be more indicative of the date of interest. Accordingly, the snippet may be associated with the February 2017 date in place of the March 2018 date. In some embodiments, documents may be analyzed relative to a particular cut-off date 460—in this case, Feb. 14, 2018—and documents associated with dates after the cutoff date may not be considered. However, using the February 2017 date rather than the March 2018 date may allow the snippet from document 450 to be included as in input to the model.

Figure 5:
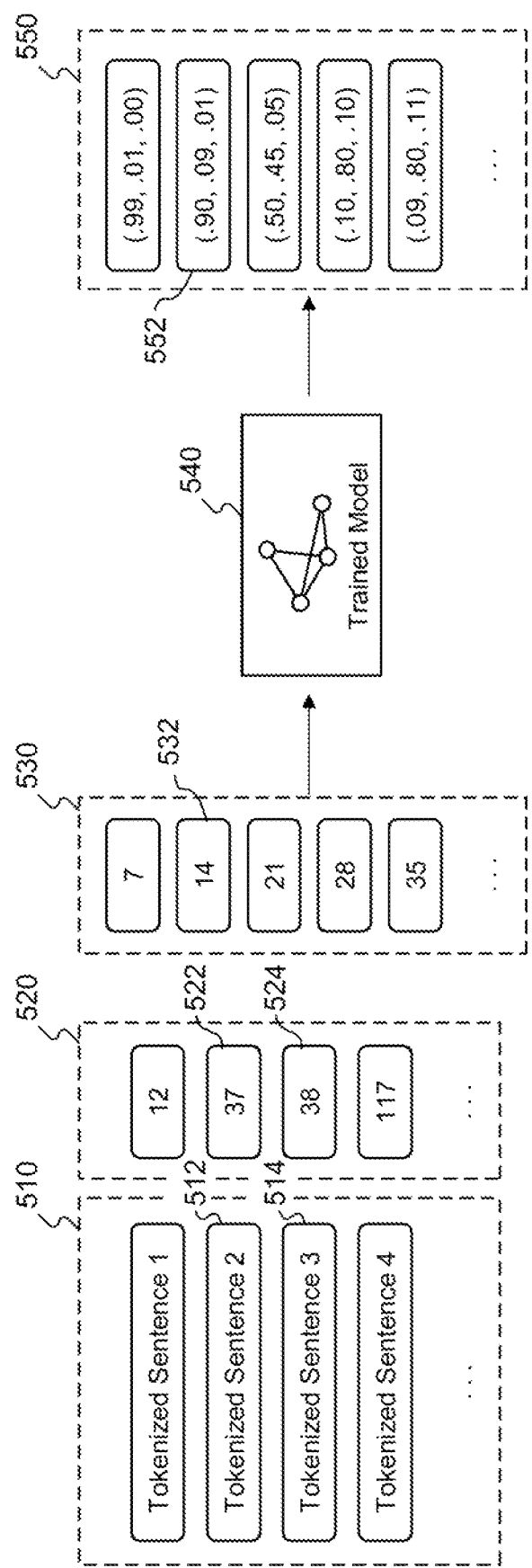
FIG. 5 is a diagrammatic illustration of an example trained model and inputs and outputs to the model, consistent with the disclosed embodiments.

The resulting input vectors and the associated input dates may be input into a trained machine learning model configured to determine a particular disease and dates associated with the event of interest. FIG. 5 is a diagrammatic illustration of an example trained model 540 and inputs and outputs to the model, consistent with the disclosed embodiments. Trained model 540 may be trained to receive, as inputs, a set of tokenized snippet vectors 510 and paired dates 520 and output probabilities 550 indicating probabilities that a particular event occurred within particular date ranges. In some embodiments, trained model (or models) 540 may include a feed forward network. Various machine learning algorithms may be used, including a neural network, a logistic regression, a linear regression, a regression, a random forest, a K-Nearest Neighbor (KNN) model (for example as described above), a K-Means model, a decision tree, a cox proportional hazards regression model, a Naïve Bayes model, a Support Vector Machines (SVM) model, a gradient boosting algorithm, or any other form of machine learning model or algorithm.

Snippet vectors 510 may represent as vectorized snippets extracted from unstructured data, as described above with respect to FIG. 3. For example, snippet vectors 510 may be represented in the form of vectorized snippets 340. Paired dates 520 may represent dates associated with each of the vectorized snippets, as described above with respect to FIG. 4. In this example, a snippet vector 512 may be associated with a paired date 522 and another snippet vector 514 may be associated with a paired date 524. Paired dates 520 may be represented in vector form, similar to snippet vectors 510. These dates may be represented in various ways. In some embodiments, this may include a standardized date format, such as YYYY/DD/MM with ("YYYY" representing a year value, "MM" representing a month value, and "DD" representing a day of the month value). In some embodiments, the dates may be represented as a number of days away from or relative to reference date, as shown in FIG. 3. For example, the dates may be expressed as a number of days before or after a cutoff date (e.g., date 460 described above), a date associated with a cohort (e.g., a cutoff date for a particular diagnosis, etc.), a current date, or any other date that may be used as a reference point.

In some embodiments, one or more query dates 530 may be input into the model in addition to snippet vectors 510 and paired dates 520. Each query date may represent a point in time that trained model 540 should make a prediction relative to. In some embodiments, the queries may be a series of dates that are evenly spaced. For example, the queries may be a series dates spaced apart by 7 days. In some embodiments, query dates 530 may be generated automatically to encompass paired dates 520. Alternatively or additionally query dates 530 may depend at least partially on an input of a user. For example, query dates 530 may each be defined manually based on an input from a user. As another example, a user may input a spacing for query dates 530 and system 130 may generate query dates 530 to encompass paired dates 520 with the spacing defined by the user. In some embodiments, this may include presenting one or more elements in a user interface (e.g., through a client device 110) and receiving an input by the user through the one or more elements of the user interface. While weekly queries are used by way of example, various other periods may be used. For example, the periods may be daily, several days, bi-weekly, monthly, yearly, or any other suitable period.

For each of query dates 530, trained model 540 may generate a prediction of whether the date of interest occurred within a range or period relative to the queried date. For example, this may include a range encompassing the query date (e.g., within 1 day, 5 days, 10 days, 30 days, or any other suitable range of the query date), a range before the query date, and a range after the query date. Accordingly, trained model 540 may output multiple probabilities associated with each of query dates 530 based on snippet vectors 510 and paired dates 520. For example, query dates 530 may include query date 532, which in this example may be a date 14 days before a reference date. Trained model 540 may output a set of probabilities 552 indicating whether a date of interest occurred before query date 532, during query date 532 (or within a range of query date 532, such as within 30 days of query date 532), or after query date 532. In the example shown, probabilities 552 may include a 90% probability of the date of interest occurring before query date 532 (or a range encompassing query date 532), a 9% probability of the date of interest occurring during query date 532 (or a range encompassing query date 532), and a 1% probability of the date of interest occurring after query date 532 (or a range encompassing query date 532). As a result, the model may generate a distribution of probabilities over the range of query dates, with each query returning a probability of whether the date of interest occurred during that query.

Figure 6:
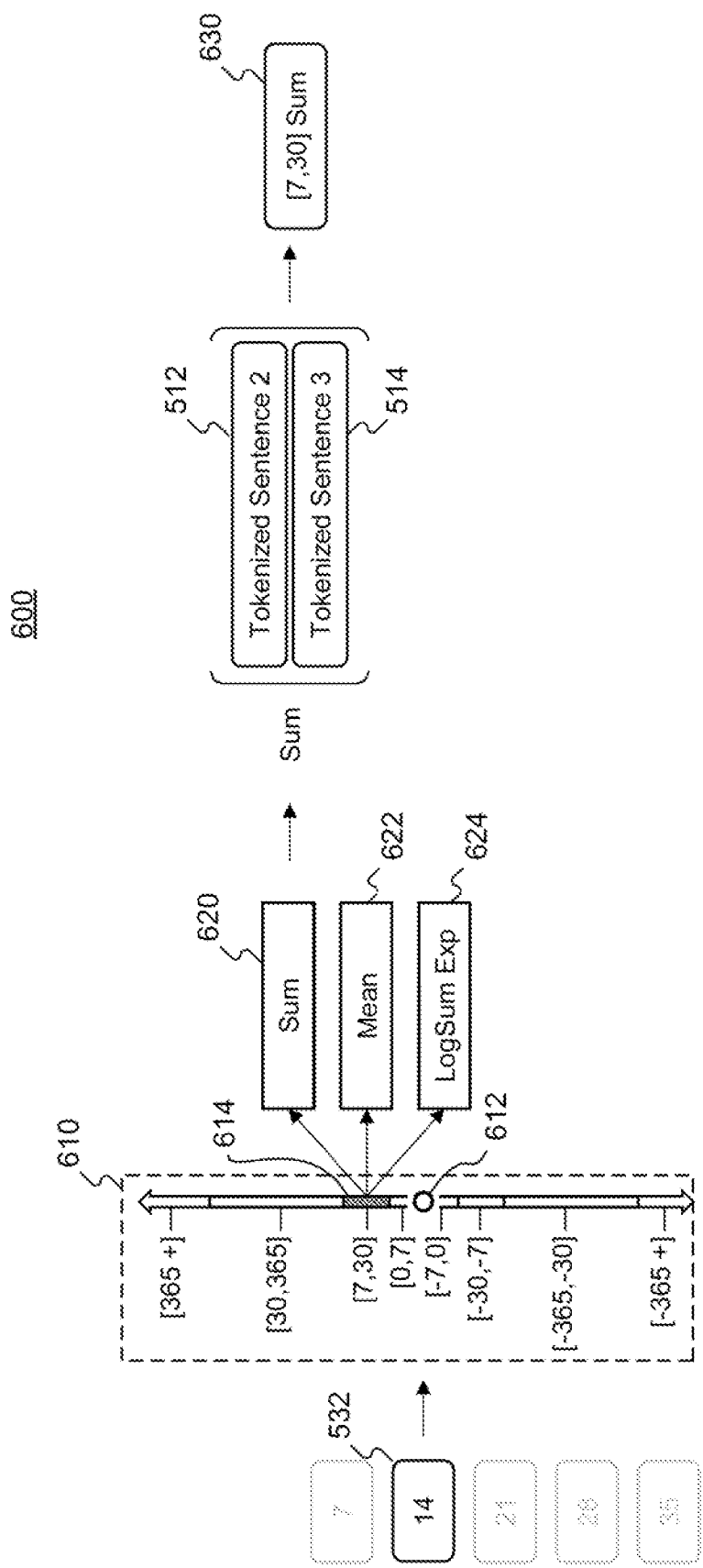
FIG. 6 is a diagrammatic illustration of an example process for determining query outputs relative to a query date, consistent with the disclosed embodiments.

In some embodiments, snippet vectors 510 may be processed further prior to being input to trained model 540. For example, to determine the probabilities for a given query (e.g., to determine probabilities 552 for query date 532), system 130 may analyze snippet vectors 510 within several time windows relative to the query. In some embodiments, this may include applying one or more aggregation functions to relevant snippets for each window. FIG. 6 is a diagrammatic illustration of an example process 600 for determining query outputs relative to a query date 532, consistent with the disclosed embodiments. In the example shown in FIG. 6, one or more query outputs 640 may be generated based on query date 532. This may include assessing snippet vectors 510 relative to a series of time windows 610, as shown. The time windows may be ranges of time relative to a reference date 612 (which corresponds to query date 532). For example, the time windows may be greater than 365 days before the query date, between 365 and 30 days before the query date, between 30 and 7 days before the query date, less than 7 days before the query date, within 7 days after the query date, between 7 and 30 days after the query date, between 30 and 365 days after the query date, and later than 365 days after the query date, as shown in FIG. 6. These time windows are provided by way of example and any other suitable time windows may be used.

For each time window, snippet vectors associated with input dates that fall within that time window may be analyzed according to one or more aggregation functions. For example, the aggregation functions may include a sum function 620, a mean function 622, and a LogSumExp function 624. Sum function 620 may represent a vector sum of the input vectors associated with dates in the time window. For example, a matrix, M, may be generated as a vector of all of the input vectors for the model. A logical matrix, D, may be generated with elements indicating whether the corresponding input vectors are included within the time window, such that a multiplication of D*M results in a sum of the relevant vectors.

In the example shown in FIG. 6, sum function 620, mean function 622, and LogSumExp function 624 are performed with respect to a time window 614. In this example, time window 614 represents a window of time ranging from 7 days after query date 532 to 30 days after query date 532. Accordingly, when applied relative to time window 614, sum function 620 will be a sum of any snippet vectors associated with dates ranging from 7 days after query date 532 to 30 days after query date 532. In this example, query date 532 is represented as a date 14 days relative to a reference date. Accordingly, time window 614 will be a range from 21 days relative to the reference date to 44 days relative to the reference date. Referring to the example snippet vectors 510 and paired dates 520 shown in FIG. 5, this will include a sum of snippet vectors 512 and 514 since paired dates 522 and 524 fall within the range defined by time window 614. As shown in FIG. 6, application of sum function 620 in time window 614 will include generating a sum of snippet vectors 512 and 514, which may result in a query output 630.

Similarly, mean function 622 may represent an average value of the input vectors associated with the time window. For example, logical matrix D may be divided by its sum along the second dimension such that multiplication of D*M results in a mean of the relevant vectors. Although not shown in FIG. 6 for purposes of simplicity, mean function 622 is applied to snippet vectors 512 and 514 to generate a corresponding query output relative to time window 614. LogSumExp function 624 may be a smooth approximation to a maximum function (i.e., a "RealSoftMax" or "TrueSoftMax" function), defined as a logarithm of the sum of the exponentials of the arguments. For example, a torch.exp( ) function may be applied to matrix M and the resulting matrix may be multiplied with logical matrix D (as D*M). A torch.log( ) function of the resulting output may be applied. LogSumExp function 624 is also applied to snippet vectors 512 and 514 to generate a corresponding query output relative to time window 614.

Each of sum function 620, mean function 622, and LogSumExp function 624 are applied with respect to each time window 610. As a result, for each time window, multiple aggregations may be generated for the input vectors associated with the time window. This may be repeated for each time window for a given query to generate an output vector for the query. This output vector may be input into a feed forward network (or similar form of recurrent neural network) to generate a probability of whether the date of interest occurred within the query date (or range of dates). While sum function 620, mean function 622, and LogSumExp function 624 are provided by way of example, one skilled in the art would recognize that different aggregation functions (or combinations of aggregation functions may be used).

Figure 7:
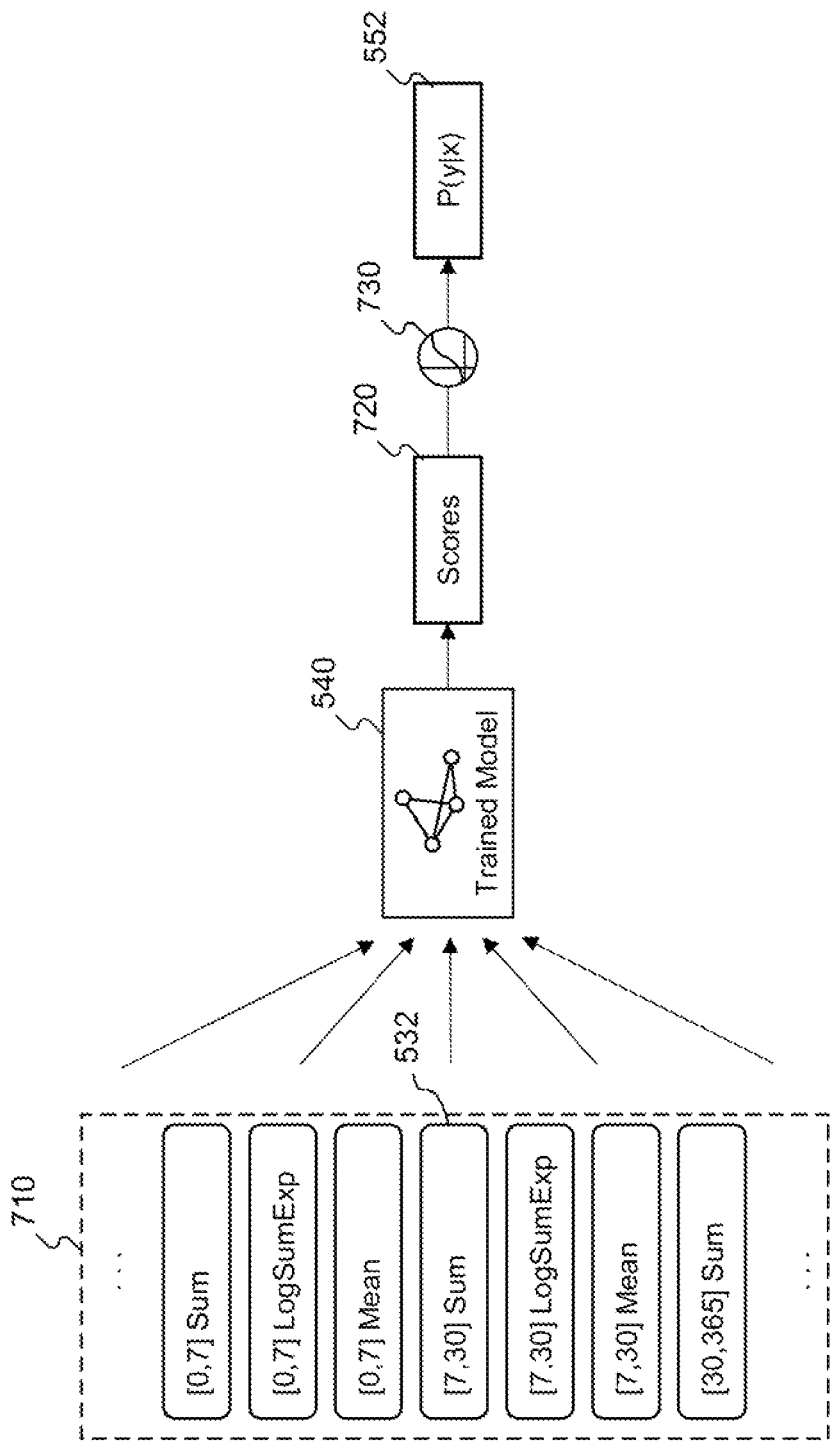
FIG. 7 is a diagrammatic illustration of an example process for generating probabilities based on a query output vector, consistent with the disclosed embodiments.

FIG. 7 is a diagrammatic illustration of an example process for generating probabilities based on a query output vector, consistent with the disclosed embodiments. As shown in FIG. 7, a query output vector 710 may be input into a model (i.e., trained model 540) to generate probabilities 552. Query output vector 710 may be generated based on application of sum function 620, mean function 622, and LogSumExp function 624 to snippet vectors 510 for each of time windows 610. In other words, for each of time windows 610, sum function 620, mean function 622, and LogSumExp function 624 may be applied to snippet vectors that are associated with paired dates that fall within the time window. For example, query output vector 710 includes query output 532, among other query outputs, as shown.

Query output vector 710 may be input to trained model 540, as shown in FIG. 7. For example, trained model may be a feed forward network (or similar form of recurrent neural network) to generate probabilities 552 relative to query date 532. Accordingly, trained model 540 may be trained using a training set of data, which may consist of a set of query output vectors generated based on snippet vectors and associated dates as described above, along with known dates of interest. This training vector may be input into a training algorithm to generate trained model 540. Accordingly, subsequent output vectors may be input into trained model 540 to generate probabilities relative to various query dates. In some embodiments, additional layers may be applied. For example, trained model 540 may output scores 720, which may be equal/not-equal scores for whether the date matches a diagnosis date or other date of interest. These scores may be real-valued, and may be converted into probabilities 552 using a Softmax function 730. The various layers illustrated in FIG. 7 are provided by way of example, and one skilled in the art would recognize other possible layers for manipulating an output of trained model 540.

Probability (or probabilities) 552 may be represented in various formats. For example, a probability may be represented as a value within a range (e.g., from 0-1, 0-100, etc.), a percentage, a value within a graduated range of values (e.g., 0, 1, 2, 3, etc.), a text-based representation of probability (e.g., low probability, high probability, etc.) or the like. In some embodiments, the model may also output a probability of the date of interest not occurring within the query date, which may be an inverse of the other probability. For example, for a given query date, the model may output a probability 0.98 of the date of interest occurring within the query date and a probability of 0.02 of the date of interest not occurring within the query date. The process above may be repeated for each query to generate a probability distribution 550 indicating a probability of when the date of interest occurred across a range of query dates. Various other outputs may be generated, such as an overall probability of the patient having been diagnosed with the particular disease, a confidence level associated with the distribution, or the like.

In some embodiments, the model may generate probabilities for multiple dates of interest. For example, continuing with the NSCLC diagnosis date example above, the model may output probabilities for each query date of whether the initial diagnosis for NSCLC occurred in that query date range and whether an advanced diagnosis (e.g., stage 3b or higher, lower stage with distant metastases, etc.) occurred in that query date range. Accordingly, for the output vector for each query, multiple feed forward layers may be applied such that multiple probabilities that are generated.

While the disclosed systems and methods are generally described using the example of particular diseases and dates associated with diagnoses and various states of the disease, it is to be understood that the same or similar processes may be performed for other event dates. For example, this may include start and end dates for a particular treatment or therapy, whether a particular drug was taken along with dosages and dates, particular diagnostics being performed and associated dates, or the like. Further, various other inputs may also be provided to the trained model, such as document types, document format, or other document metadata.

In some embodiments, the model may be trained by identifying a cohort of patients having a particular disease, identifying different stages of the disease and relevant diagnosis dates. For example, input to a model may include a set of sentences containing keywords related to advanced NSCLC and extracted from a patient's EHR documents. Each sentence may be associated with a date, using the document timestamp or, if present, a date mentioned explicitly in the sentence. The sentences may be processed by a GRU networks may be trained to predict the probability of each diagnosis for a sequence of time points, which can then used to extract whether the patient had been diagnosed with a particular disease and the diagnosis date(s) if so.

In some embodiments, the model may be trained for both diagnoses of a disease and treatment. For example, input to a model may include one or more sentences having keywords related to diagnosis of the disease as well as sentences having keywords related to treatment of the disease. The input may also include a training data set of dates associated with the diagnosis and treatment of the disease. For example, the training data set may include dates when the disease (or various stages of the disease) was diagnosed. Further, the training data set may include dates when particular lines of treatment began, as well as other dates associated with treatment (e.g., an increase in dosage, a change in treatment, etc.). The model may be trained using stochastic gradient descent or similar methods for training a model using a set of labeled training data. As a result, the trained model may be configured to extract a particular disease and/or treatment type, as well as dates associated with the diagnosis and treatment of the disease.

Figure 8:
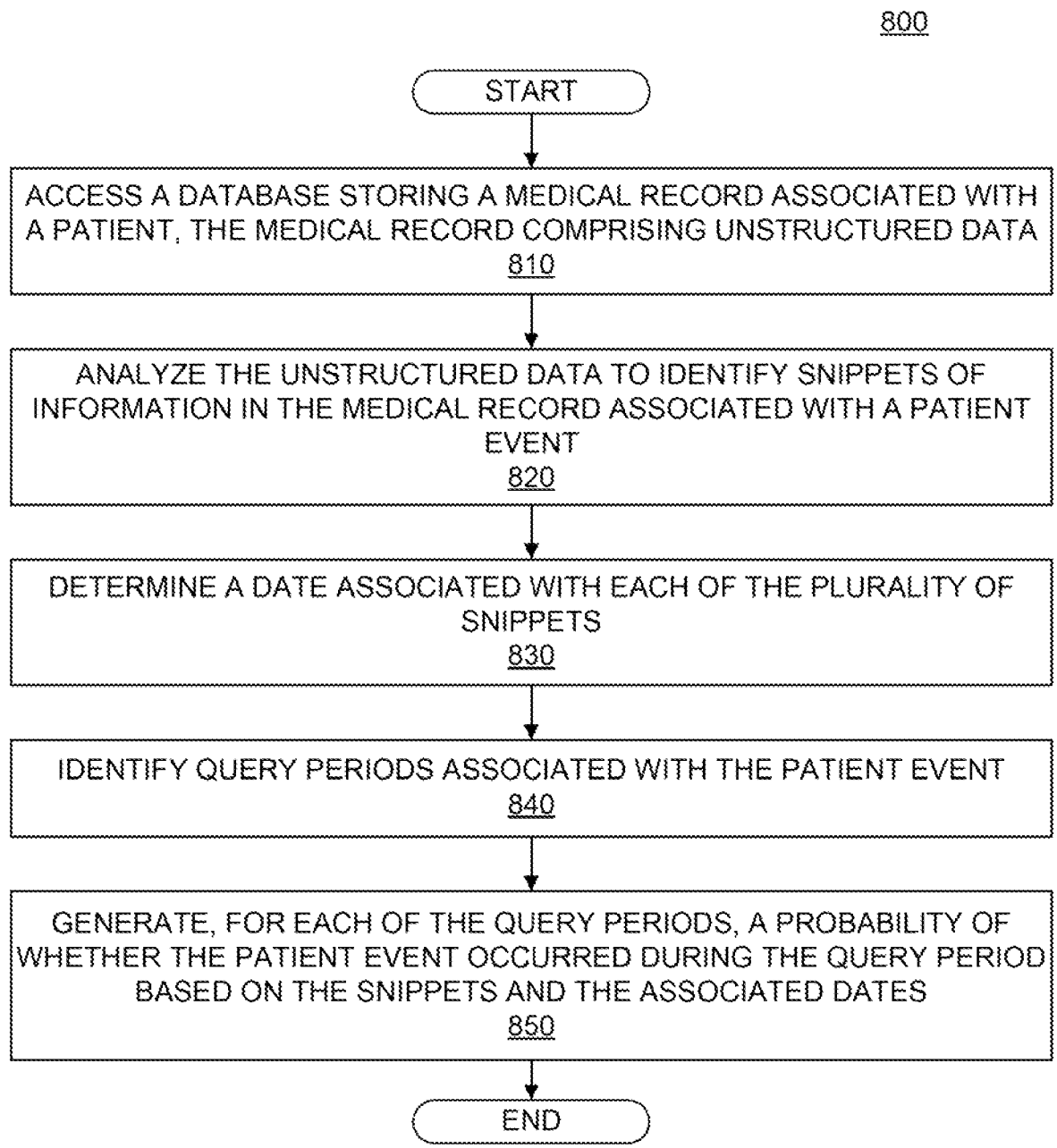
FIG. 8 is a flowchart showing an example process for extracting patient information, consistent with the disclosed embodiments.

FIG. 8 is a flowchart showing an example process 800 for extracting patient information, consistent with the disclosed embodiments. Process 800 may be performed by at least one processing device, such as processing engine 131, as described above. It is to be understood that throughout the present disclosure, the term "processor" is used as a shorthand for "at least one processor." in other words, a processor may include one or more structures that perform logic operations whether such structures are collocated, connected, or dispersed. In some embodiments, a non-transitory computer readable medium may contain instructions that when executed by a processor cause the processor to perform process 800. Further, process 800 is not necessarily limited to the steps shown in FIG. 8, and any steps or processes of the various embodiments described throughout the present disclosure may also be included in process 800, including those described above with respect to FIGS. 3, 4, 5, 6, and 7.

In step 810, process 800 includes accessing a database storing a medical record associated with a patient. For example, system 130 may access patient medical records from local database 132 or from an external data source, such as data sources 120. The medical record may comprise one or more electronic files, such as text files, image files, PDF files, XLM files, YAML files, or the like. The one or more medical records may correspond to medical record 200 discussed above. In some embodiments, the medical record may include unstructured data, such as unstructured data 210.

In step 820, process 800 includes analyzing the unstructured data to identify a plurality of snippets of information in the medical record associated with a patient event. For example, this may include identifying snippet 332 as described above. As described above, the patient event may be any event that may be associated with the care of a patient. For example, the patient event may include at least one of a diagnosis date, a treatment date, or an operation date. In some embodiments, process 800 may further include generating a plurality of snippet vectors based on the snippets, such as snippet vectors 510.

In step 830, process 800 includes determining a date associated with each of the plurality of snippets. For example, this may include determining paired dates 520, as described above. In some embodiments, determining the date associated with each of the plurality of snippets may include identifying a date based on metadata of a document a snippet is included in. For example, as described above with respect to FIG. 4, this may include a date a document was created, saved, published, or various other dates associated with a document. Alternatively or additionally, determining the date associated with each of the plurality of snippets includes identifying a date referenced in the snippet. For example, a snippet itself may include a date which may be more reflective of a diagnosis date or other event discussed in the snippet.

In step 840, process 800 includes identifying a plurality of query periods associated with the patient event. For example, this may include determine query dates 530 as described above. Accordingly, identifying the plurality of query periods includes identifying a plurality of query dates and the plurality of query periods include at least one period relative to each of the query dates. For example, the at least one period relative to each of the query dates may include a period encompassing the query date, a period before the query date, and a period after the query date. The query dates may be identified in various ways. In some embodiments, the plurality of query dates may be dates spaced apart by one week, although any other suitable spacing may be used. In some embodiments, the query dates, a range of the query dates, a spacing of the query dates, or various other factors may be specified by a user input, as described above. Accordingly, identifying a plurality of query periods associated with the patient event may include receiving at least one user input associated with the query periods via a user interface. For example, the user interface may be displayed on client device 110, as described above.

In step 850, process 800 includes generating, for each of the query periods, a probability of whether the patient event occurred during the query period based on the plurality of snippets and the associated dates. For example, this may include generating probabilities 550, as described above. In some embodiments, this may include various steps described with respect to FIGS. 6 and 7. For example, step 850 may include evaluating the plurality of snippets over a plurality of time windows relative to each of the plurality of query dates, such as time windows 610. In some embodiments, evaluating the plurality of snippets over a plurality of time windows may include, for each of the plurality of time windows, processing snippets associated with a date falling within the time window using one or more aggregation functions, as described in further detail above with respect to FIG. 6. For example, the one or more aggregation functions include at least one of a sum function, a mean function, or a LogSumExp function. Step 850 may further include inputting a result of the plurality of functions (i.e., query output vector 710) into a feed forward network or other form of trained machine learning model.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted system for determining a patient event date, the system comprising:
at least one processor programmed to:
access a database storing a medical record associated with a patient, the medical record comprising unstructured data;
analyze the unstructured data to identify a plurality of snippets of information in the medical record associated with a patient event;
determine a date associated with each of the plurality of snippets;
generate a plurality of snippet vectors based on the plurality of snippets, wherein generating the plurality of snippet vectors includes replacing at least one term within the plurality of snippets with a tokenized representation of the term;
identify a plurality of query periods associated with the patient event;
for each query period, apply a plurality of aggregation functions to the plurality of snippet vectors and the associated dates to generate a plurality of query outputs, the plurality of aggregation functions comprising at least:
a first function representing a sum of the plurality of snippet vectors relative to at least one time window;
a second function representing an average of the plurality of snippet vectors relative to the at least one time window; and
a third function relative to the at least one time window, the third function being different from the first function and the second function and including a smooth approximation function; and
generate, for each of the query periods, a probability of whether the patient event occurred during the query period based on the query outputs.

2. The model-assisted system of claim 1, wherein the patient event comprises at least one of a diagnosis date, a treatment date, or an operation date.

3. The model-assisted system of claim 1, wherein determining the date associated with each of the plurality of snippets includes identifying a date based on metadata of a document a snippet is included in.

4. The model-assisted system of claim 1, wherein determining the date associated, with each of the plurality of snippets includes identifying a date referenced in the snippet.

5. The model-assisted system of claim 1, wherein identifying the plurality of query periods includes identifying a plurality of query dates and wherein the plurality of query periods include at least one period relative to each of the query dates.

6. The model-assisted system of claim 5, wherein the at least one period relative to each of the query dates includes a period encompassing the query date, a period before the query date, and a period after the query date.

7. The model-assisted system of claim 5, wherein the plurality of query dates comprise dates spaced apart by one week.

8. The model-assisted system of claim 5, wherein generating the probability includes evaluating the plurality of snippets over a plurality of time windows relative to each of the plurality of query dates.

9. The model-assisted system of claim 8, wherein evaluating the plurality of snippets over a plurality of time windows includes, for each time window of the plurality of time windows, processing snippets associated with a date failing within the time window using the plurality of aggregation functions.

10. The model-assisted system of claim 1, wherein the smooth approximation function includes a LogSumExp function.

11. The model-assisted system of claim 9, wherein generating the probability includes inputting a result of the plurality of aggregation functions into a feed forward network.

12. A method for determining a patient event date, the method comprising:
- accessing a database storing a medical record associated with a patient, the medical record comprising unstructured data;
- analyzing the unstructured data to identify a plurality of snippets of information in the medical record associated with a patient event;
- determining a date associated with each of the plurality of snippets;
- generating a plurality of snippet vectors based on the plurality of snippets, wherein generating the plurality of snippet vectors includes replacing at least one term within the plurality of snippets with a tokenized representation of the term;
- identifying a plurality of query periods associated with the patient event;
- for each query period, applying a plurality of aggregation functions to the plurality of snippet vectors and the associated dates to generate a plurality of query outputs, the plurality of aggregation functions comprising at least:
  - a first function representing a sum of the plurality of snippet vectors relative to at least one time window;
  - a second function representing an average of the plurality of snippet vectors relative to the at least one time window; and
  - a third function relative to the at least one time window, the third function being different from the first function and the second function and including a smooth approximation function; and
- generating, for each of the query periods, a probability of whether the patient event occurred during the query period based on the query outputs.

13. The method of claim 12, wherein the patient event comprises at least one of a diagnosis date, a treatment date, or an operation date.

14. The method of claim 12, wherein identifying the plurality of query periods includes identifying a plurality of query dates and wherein the plurality of query periods include at least one period relative to each of the query dates.

15. The method of claim 14, wherein the at least one period relative to each of the query dates includes at least one period encompassing the query date, at least one period before the query date, and at least one period after the query date.

16. The method of claim 14, wherein generating the probability includes evaluating the plurality of snippets over a plurality of time windows relative to each of the plurality of query dates.

17. The method of claim 16, wherein evaluating the plurality of snippets over a plurality of time windows includes, for each of the plurality of time windows, processing the snippets associated with a date falling within the time window using the plurality of aggregation functions.

18. The method of claim 12, wherein the third function includes a LogSumExp function.

19. A non-transitory computer-readable medium comprising instructions that, when executed by one or more processors, cause the one or more processors to perform a method for determining a patient event date, the method comprising;
- accessing a database storing a medical record associated with a patient, the medical record comprising unstructured data;
- analyzing the unstructured data to identify a plurality of snippets of information in the medical record associated with a patient event;
- determining a date associated with each of the plurality of snippets;
- generating a plurality of snippet vectors based on the plurality of snippets, wherein generating the plurality of snippet vectors includes replacing at least one term within the plurality of snippets with a tokenized representation of the term;
- identifying a plurality of query periods associated with the patient event;
- for each query period, applying a plurality of aggregation functions to the plurality of snippet vectors and the associated dates to generate a plurality of query outputs, the plurality of aggregation functions comprising at least:
  - a first function representing a sum of the plurality of snippet vectors relative to at least one time window;
  - a second function representing an average of the plurality of snippet vectors relative to the at least one time window; and
  - a third function relative to the at least one time window, the third function being different from the first function and the second function and including a smooth approximation function; and
- generating, for each of the query periods, a probability of whether the patient event occurred during the query period based on the query outputs.

\* \* \* \* \*